United States Patent [19]
Miller et al.

[11] Patent Number: 5,817,893
[45] Date of Patent: Oct. 6, 1998

[54] PROCESSES FOR THE MANUFACTURE AND PURIFICATION OF 1,1,2,2,3,3,4,4-OCTAFLUOROBUTANE AND BY-PRODUCTS

[75] Inventors: Ralph Newton Miller, Newark; V. N. Mallikarjuna Rao, Wilmington, both of Del.; Allen Capron Sievert, Elkton, Md.

[73] Assignee: E. I. du Pont de Nemours and Company, Wilmington, Del.

[21] Appl. No.: 868,349

[22] Filed: Jun. 3, 1997

Related U.S. Application Data

[60] Provisional application No. 60/019,993 Jun. 18, 1996.
[51] Int. Cl.⁶ ................................................ C07C 19/08
[52] U.S. Cl. ............................................... 570/134
[58] Field of Search ...................................... 570/134

[56] References Cited

U.S. PATENT DOCUMENTS

| | | | |
|---|---|---|---|
| 3,651,019 | 3/1972 | Asscher et al. | 260/77.2 |
| 5,120,883 | 6/1992 | Rao et al. | 570/123 |
| 5,194,170 | 3/1993 | Merchant et al. | 252/67 |
| 5,221,493 | 6/1993 | Merchant et al. | 252/67 |
| 5,250,208 | 10/1993 | Merchant et al. | 252/67 |
| 5,346,595 | 9/1994 | Clemmer et al. | 203/75 |
| 5,446,217 | 8/1995 | Van Der Puy et al. | 570/156 |

FOREIGN PATENT DOCUMENTS

| | | | |
|---|---|---|---|
| 0 669 303 | 1/1995 | European Pat. Off. | C07C 17/38 |
| 0 703 205 A1 | 8/1995 | European Pat. Off. | C07C 17/20 |
| WO 94/19301 | 9/1994 | WIPO | C07C 17/38 |
| WO 95/04021 | 2/1995 | WIPO | C07C 17/20 |
| WO 95/04022 | 2/1995 | WIPO | C07C 17/23 |
| WO 96/01797 | 7/1995 | WIPO | C07C 17/20 |
| WO 97/05089 | 2/1997 | WIPO | C07C 17/278 |

*Primary Examiner*—Bernard Dentz

[57] ABSTRACT

A process is disclosed for producing 1,12,2,3,3,4,4-octafluorobutane. The process involves chlorination of 2,2,3,3-tetrafluorobutane to form a mixture of chloro-compounds wherein compounds of the formula $C_4H_4Cl_{6-x}F_4$ (where x is 0 or 1) comprise at least 50 mole % of the mixture of chloro-compounds, followed by hydrofluorination, then hydrogenolysis, and sufficient recycle to provide a selectivity to $CHF_2CF_2CF_2CHF_2$ of at least about 75% based upon the moles of $CH_3CF_2CF_2CH_3$ reacted. Also disclosed is a multi-distillation process for the purification of $CHF_2CF_2CF_2CHF_2$ from a mixture of HF and the compound(s). Also disclosed are certain new halogenated butanes containing fluorine, and a composition which contains HF in combination with an effective amount of $CHF_2CF_2CF_2CHF_2$ to form an azeotrope or azeotrope-like composition with hydrogen fluoride.

16 Claims, 1 Drawing Sheet

PROCESSES FOR THE MANUFACTURE AND PURIFICATION OF 1,1,2,2,3,3,4,4-OCTAFLUOROBUTANE AND BY-PRODUCTS

This application derives priority from Verified Provisional application Ser. No. 60/019,993 filed Jun. 18, 1996.

FIELD OF THE INVENTION

This invention relates to the manufacture of 1,1,2,2,3,3,4,4-octafluorobutane, its azeotropic compositions with hydrogen fluoride and their use in separation processes.

BACKGROUND

Chlorofluorocarbons (CFCs, i.e., compounds containing only carbon, fluorine and chlorine) have been used for many years as refrigerants, heat transfer media, foam expansion agents, aerosol propellants, solvents, fire extinguishants and power cycle working fluids. For example, various CFC solvents have been used as cleaning liquids for the removal of contaminants from contaminated articles and materials. Certain fluorine-containing organic compounds such as 1,1,2-trichloro-1,2,2-trifluoroethane (CFC-113) have been reported as useful for this purpose, particularly with regard to cleaning organic polymers and plastics which may be sensitive to other more common and more powerful solvents such as trichloroethylene or perchloroethylene. Recently, however, there have been efforts to reduce the use of certain compounds such as trichlorotrifluoroethane which also contain chlorine because of a concern over their potential to deplete ozone. Consequently, there is a worldwide effort to find alternative compounds.

The properties of halogenated hydrocarbons can be influenced by the arrangement of the halogens (and hydrogen, when present) on the carbon framework. One of the challenges in preparing compounds containing fluorine and hydrogen has been to achieve the desired arrangement of such substituents. When more than one hydrogen is present in the molecule, one arrangement involves providing a hydrogen on different carbons spaced a selected distance from one another along a carbon chain. For example, in a compound of the formula $C_4H_2F_8$, it can be desirable to provide a hydrogen substituent on each of two carbon atoms which are separated from one another by a chain of two other carbon atoms. 1,1,2,2,3,3,4,4-Octafluorobutane (i.e., $CHF_2CF_2CF_2CHF_2$ or HFC-338pcc) is such a compound. HFC-338pcc forms useful blends, and particularly azeotropes, with solvents such as alcohols, ketones, and other halogenated solvents to form compositions useful for cleaning surfaces, especially electronic components as disclosed in U.S. Pat. Nos. 5,250,208, 5,221,493 and 5,194,170. There is a need for non-chlorinated solvents like HFC-338pcc (which have little effect on the ozone layer) as replacements for more chlorinated solvents such as CFC-113.

SUMMARY OF THE INVENTION

A process is provided for producing 1,1,2,2,3,3,4,4-octafluorobutane (i.e., $CHF_2CF_2CF_2CHF_2$ or HFC-338pcc). The process comprises (a) reacting a mixture comprising 2,2,3,3-tetrafluorobutane (i.e., $CH_3CF_2CF_2CH_3$ or HFC-374scc) and chlorine to form a mixture of chloro-compounds selected from the group consisting of $CCl_3(CF_2)_2CCl_3$ (CFC-314jcc), $CHCl_2(CF_2)_2CCl_3$ (HCFC-324jcc), $CH_2Cl(CF_2)_2CCl_3$ (HCFC-334jcc), $CH_3(CF_2)_2CCl_3$ (HCFC-344jcc), $CH_3(CF_2)_2CHCl_2$ (HCFC-354ncc) and $CH_3(CF_2)_2CH_2Cl$ (HCFC-364occ) wherein compounds of the formula $C_4H_xCl_{6-x}F_4$ (where x is 0 or 1) comprise at least about 50 mole % of said mixture of chloro-compounds; (b) contacting a mixture comprising compounds of the formula $C_4H_xCl_{6-x}F_4$ from (a) and hydrogen fluoride (HF) with a fluorination catalyst to form a mixture of fluoro-compounds selected from the group consisting of $CCl_2F(CF_2)_2CCl_3$, $CCl_2F(CF_2)_2CCl_2F$, $CCl_2F(CF_2)_2CClF_2$, $CClF_2(CF_2)_2CClF_2$, $CClF_2(CF_2)_2CF_3$, $CHCl_2(CF_2)_2CCl_2F$, $CHClF(CF_2)_2CCl_3$, $CHCl_2(CF_2)_2CClF_2$, $CHClF(CF_2)_2$ $CCl_2F$, $CHF_2(CF_2)_2CCl_3$, $CHClF(CF_2)_2CClF_2$, $CHF_2(CF_2)_2CCl_2F$, $CHCl_2(CF_2)_2CF_3$, $CHClF(CF_2)_2CF_3$, $CHF_2(CF_2)_2CClF_2$ and $CHF_2(CF_2)_2CF_3$ wherein compounds of the formula $C_4H_{2-y}Cl_yF_8$ (where y is 1 or 2) comprise at least about 10 mole % of said mixture of fluoro-compounds; and (c) contacting a mixture comprising compounds of the formula $C_4H_{2-y}Cl_yF_8$ from (b) and hydrogen with a hydrogenolysis catalyst to produce $CHF_2CF_2CF_2CHF_2$. Sufficient chloro-compounds formed in (a) are recycled to the chlorination of (a) and sufficient fluoro-compounds formed in (b) are recycled to the chlorination of (a) or the fluorination of (b) to provide a selectivity to $CHF_2CF_2CF_2CHF_2$ of at least about 75% based upon the moles of $CH_3CF_2CF_2CH_3$ reacted in (a).

This invention also provides a process for the purification of at least one compound selected from the group consisting of $CCl_2F(CF_2)_2CCl_3$, $CCl_2F(CF_2)_2CCl_2F$, $CCl_2F(CF_2)_2CClF_2$, $CClF_2(CF_2)_2CClF_2$, $CClF_2(CF_2)_2CF_3$, $CHCl_2(CF_2)_2CCl_2F$, $CHClF(CF_2)_2CCl_3$, $CHCl_2(CF_2)_2CClF_2$, $CHClF(CF_2)_2CCl_2F$, $CHF_2(CF_2)_2CCl_3$, $CHClF(CF_2)_2CClF_2$, $CHF_2(CF_2)_2CCl_2F$, $CHCl_2(CF_2)_2CF_3$, $CHClF(CF_2)_2CF_3$, $CHF_2(CF_2)_2CClF_2$, $CHF_2CF_2CF_2CHF_2$, $CHF_2CF_2CF_2CH_2F$, $CHF_2CF_2CF_2CF_3$ and $CH_2FCF_2CF_2CF_3$ from a mixture comprising HF and said at least one compound. The purification process comprises (a) subjecting the mixture of HF and said at least one compound to a distillation step in which a composition enriched in either (i) HF or (ii) said at least one compound is removed as a first distillate with the bottoms being enriched in the other of said components (i) or (ii); (b) subjecting said first distillate to an additional distillation conducted at a different pressure in which the component enriched as bottoms in (a) is removed as a second distillate with the bottoms of the additional distillation enriched in the components enriched in the first distillate; and (c) recovering said at least one compound essentially free of HF as bottoms from either the distillation of (a) or the distillation of (b).

New compounds provided in accordance with this invention include $CCl_2FCF_2CF_2CClF_2$, $CCl_3CF_2CF_2CCl_2F$, $CHCl_2CF_2CF_2CCl_3$, $CHCl_2CF_2CF_2CCl_2F$, $CHClFCF_2CF_2CCl_3$, $CHCl_2CF_2CF_2CClF_2$, $CHClFCF_2CF_2CCl_2F$, $CHF_2CF_2CF_2CCl_3$, $CHF_2CF_2CF_2CCl_2F$, $CHClFCF_2CF_2CF_3$, $CH_3CF_2CF_2CH_2Cl$ and $CH_2ClCF_2CF_2CCl_3$. These compounds are useful as intermediates for producing hydrofluorocarbons.

Also provided are compositions which comprise hydrogen fluoride in combination with an effective amount of $CHF_2CF_2CF_2CHF_2$ to form an azeotrope or azeotrope-like composition with hydrogen fluoride, said composition containing from about 3.5 to 36.8 mole percent $CHF_2CF_2CF_2CHF_2$.

DETAILED DESCRIPTION

Figure 1:
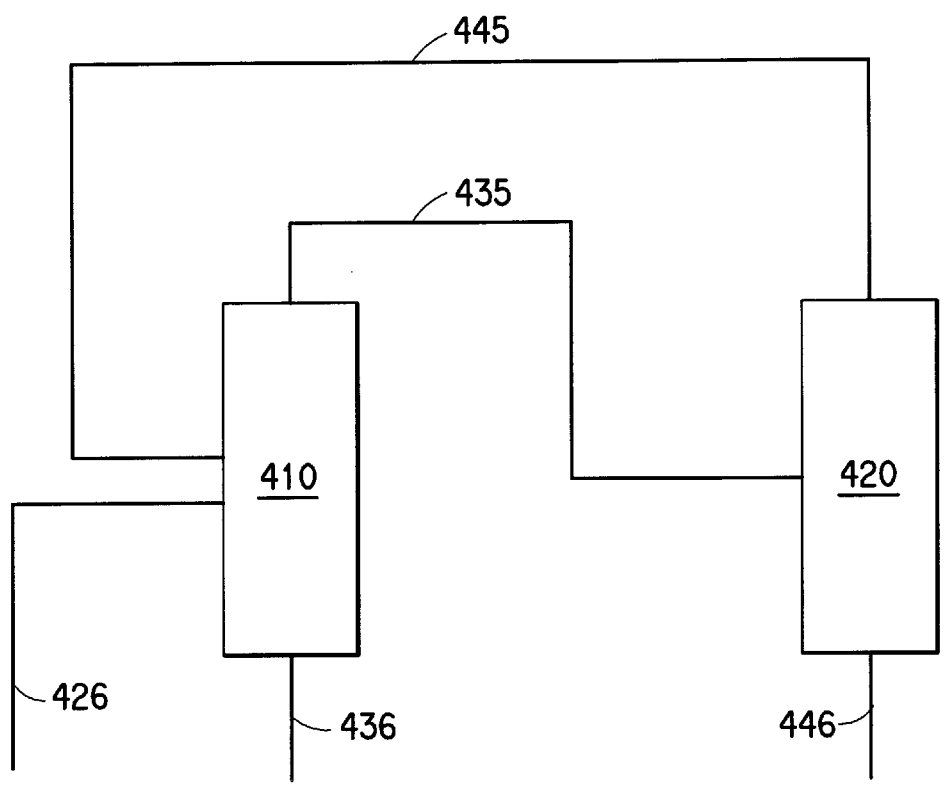
FIG. 1 is a schematic flow diagram of an embodiment of the purification process of this invention, namely an azeotrope separation process.

The present invention includes a process for the separation of an azeotropic mixture of hydrogen fluoride (HF) and 1,1,2,2,3,3,4,4-octafluorobutane (i.e., $CHF_2CF_2CF_2CHF_2$ or HFC-338pcc) to obtain $CHF_2CF_2CF_2CHF_2$ essentially free of HF. For example, (a) an initial mixture wherein the molar ratio of HF to HFC-338pcc is greater than about 3:1 can be separated by azeotropic distillation in a first distillation column wherein the temperature of the feed inlet to said distillation column is about 102° C. and the pressure is about 216 psia (1490 kPa), with azeotrope products containing HF and HFC-338pcc being removed as distillate from the top of the first distillation column and HF being removed from the bottom of the first distillation column; (b) said azeotrope products from the top of the column in step (a) can be fed to a second distillation column wherein the temperature of the feed inlet to said second distillation column is about 41° C. and the pressure is about 21.2 psia (146 kPa), with azeotrope products containing HF and HFC-338pcc being removed as distillate from the top of the second distillation column; and (c) essentially pure HFC-338pcc can be recovered from the bottom of the second distillation column in step (b). Optionally, said azeotrope products containing HF and HFC-338pcc removed from the top of the second distillation column can be recycled as feed to step (a).

In another embodiment of this invention, (a) an initial mixture wherein the molar ratio of HF to HFC-338pcc is about 3:1 or less, can be separated by azeotropic distillation in a first distillation column wherein the temperature of the feed inlet to said distillation column is about 41° C. and the pressure is about 21.2 psia (146 kPa) with azeotrope products containing HF and HFC-338pcc being removed as distillate from the top of the first distillation column; (b) said azeotrope products from the top of the column in step (a) can be fed to a second distillation column wherein the temperature of the feed inlet to said second distillation column is about 101° C. and the pressure is about 216 psia (1490 kPa), with azeotrope products containing HF and HFC-338pcc being removed as distillate from the top of the second distillation column and HF being removed from the bottom of the second distillation column; and (c) essentially pure HFC-338pcc can be recovered from the bottom of the first distillation column. Optionally, said azeotrope products containing HF and HFC-338pcc from the top of the second distillation column can be recycled as feed to step (a).

The above embodiments of this invention involve azeotropic distillation of mixtures of HF and $CHF_2CF_2CF_2CHF_2$ (HFC-338pcc). The product mixtures distilled in accordance with this invention can be obtained from a variety of sources. These sources include product mixtures from the following sequence of reactions.

$CH_3CF_2CF_2CH_3$ (HFC-374scc), a compound known in the art, can be contacted with chlorine (e.g., in the vapor phase) in the presence of a chlorination catalyst. The catalyst for the chlorination may be composed of activated carbon alone or carbon with a chloride and/or fluoride of a metal selected from the group consisting of zinc, copper, chromium, ruthenium, rhodium, platinum and mixtures thereof. Under reaction conditions the metal halides may be in the form of mixed metal halides (e.g., a chlorofluoride). Additional details for the catalytic chlorination of a hydrofluorocarbon such as HFC-374scc are disclosed in U.S. Pat. No. 5,120,883. Alternatively, HFC-374scc may be chlorinated in the liquid phase in the presence of a source of ultraviolet radiation and optionally in the presence of a solvent. Such a technique is well known in the art; see for example, the article by Poustma in "Free Radicals" (Wiley: New York, 1973), J. K. Kochi, ed., pp. 159–229.

The chlorination may be run such that products of this chlorination reaction consist essentially of $CCl_3CF_2CF_2CCl_3$ (CFC-314jcc), $CHCl_2CF_2CF_2CCl_3$ (HCFC-324jcc) and HCl. For example, at least 6 moles of chlorine can be contacted with HFC-374scc for a time sufficient to yield products consisting essentially of CFC-314jcc and HCFC-324jcc. HCFC-324jcc is a new composition of matter. Intermediates produced in the chlorination of $CH_3CF_2CF_2CH_3$ include $CH_3CF_2CF_2CH_2Cl$, $CH_3CF_2CF_2CHCl_2$, $CH_3CF_2CF_2CCl_3$, and $CH_2ClCF_2CF_2CCl_3$. Said intermediates are generally lower boiling than $CCl_3CF_2CF_2CCl_3$ (CFC-314jcc) and $CHCl_2CF_2CF_2CCl_3$ (HCFC-324jcc) and can be separated therefrom by distillation and can be recycled to the chlorination reactor. Among the chlorination intermediates, $CH_3CF_2CF_2CH_2Cl$ (HCFC-364occ) and $CH_2ClCF_2CF_2CCl_3$ (HCFC-334jcc) are new compositions of matter. The mixture of CFC-314jcc and HCFC-324jcc is contacted with at least a stoichiometric amount of HF, based on the moles of CFC-314jcc, in the gaseous phase in the presence of vapor phase fluorination catalysts (preferably after removal of HCl).

Vapor phase fluorination catalysts which may be used include metal oxides and/or other metal salts which are either supported or unsupported. Suitable supports include fluorided alumina, aluminum fluoride and carbon. Catalysts comprising trivalent chromium either supported or unsupported are preferred. Other preferred catalysts are metal halides supported on either fluorided alumina, aluminum fluoride or carbon. The preferred metal halides include those derived from cobalt, nickel, magnesium and copper. Combinations of metal compounds such as those derived from Cr and Mg, Cr and Zn, Cr and Co, and Cr and Ni can also be used advantageously. Preferably, when used with a support, the total metal content of the catalyst will be from about 0.1 to 20 percent by weight; typically, from about 0.1 to 10 percent by weight.

Fluorided alumina and aluminum fluoride can be prepared as described in U.S. Pat. No. 4,902,838. Metal halides on aluminum fluoride and metal halides on fluorided alumina can be prepared by procedures described in U.S. Pat. No. 4,766,260. Catalysts comprising chromium are well known in the art (see e.g., U.S. Pat. No. 5,036,036). Chromium supported on alumina can be prepared as described in U.S. Pat. No. 3,541,165. Chromium supported on carbon can be prepared as described in U.S. Pat. No. 3,632,834. Catalysts comprising chromium and magnesium may be prepared as described in Canadian Patent No. 2,025,145. Other supported metal halides can be prepared in a similar manner to those disclosed in the above patents.

The fluorination reactor products can include $CCl_2FCF_2CF_2CCl_3$ (CFC-315jcc), $CCl_2FCF_2CF_2CCl_2F$ (CFC-316kcc), $CCl_2FCF_2CF_2CClF_2$ (CFC-317lcc), $CClF_2CF_2CF_2CClF_2$ (CFC-318lcc), $CClF_2CF_2CF_2CF_3$ (CFC-319l), $CHCl_2CF_2CF_2CCl_2F$ (HCFC-325kcc), $CHClFCF_2CF_2CCl_3$ (HCFC-325jcc), $CHCl_2CF_2CF_2CClF_2$ (HCFC-326lcc), $CHClFCF_2CF_2CCl_2F$ (HCFC-326kcc), $CHF_2CF_2CF_2CCl_3$ (HCFC-326jcc), $CHF_2CF_2CF_2CCl_2F$ (HCFC-327kcc), $CHClFCF_2CF_2CClF_2$ (HCFC-327lcc), $CHCl_2CF_2CF_2CF_3$ (HCFC-327n), $CHF_2CF_2CF_2CClF_2$ (HCFC-328lcc), $CHClFCF_2CF_2CF_3$ (HCFC-328r), $CHF_2CF_2CF_2CF_3$ (HFC-329p), HCl and HF. Higher boiling products such as CFC-315jcc, CFC-316kcc, HCFC-325kcc, HCFC-325jcc, HCFC-326lcc, HCFC-326kcc, and HCFC-326jcc can be separated from the other fluorination reactor products (e.g., by distillation) and recycled to the fluorination reactor or to the chlorination reactor. The fluorination reactor product mixture, optionally containing HF, is contacted with hydrogen in the presence of a hydrogenolysis catalyst, preferably, after removal of HCl. The hydrogenolysis of (c) can be done in the vapor phase over a Group VIII metal catalyst, preferably palladium, rhodium or ruthenium. Pd and Rh are the more preferred metals, with palladium being most preferred. The metal catalyst may be supported (e.g., on carbon, alumina, aluminum fluoride, fluorided alumina or chromium oxide). $CHF_2CF_2CF_2CH_2F$, $CHF_2CF_2CF_2CF_3$, and $CH_2FCF_2CF_2CF_3$ are typical by-products of (c).

Among the fluorination products, $CCl_2FCF_2CF_2CClF_2$, $CCl_3CF_2CF_2CCl_2F$, $CHCl_2CF_2CF_2CCl_2F$, $CHClFCF_2CF_2CCl_3$, $CHCl_2CF_2CF_2CClF_2$, $CHClFCF_2CF_2CCl_2F$, $CHF_2CF_2CF_2CCl_3$, $CHF_2CF_2CF_2CCl_2F$, and $CHClFCF_2CF_2CF_3$ are new compositions of matter.

Of note are embodiments where $CClF_2CF_2CF_2CF_3$, $CClF_2CF_2CF_2CClF_2$, $CCl_2FCF_2CF_2CClF_2$, $CHF_2CF_2CF_2CClF_2$, $CHClFCF_2CF_2CF_3$, $CHClCF_2CF_2CClF_2$, $CHF_2CF_2CF_2CCl_2F$, $CHCl_2CF_2CF_2CF_3$ and $CHF_2CF_2CF_2CF_3$ from (b) are all fed to (c). The hydrogenolysis reactor effluent then typically includes $CHF_2CF_2CF_2CHF_2$ (HFC-338pcc), HF, HCl and much lesser amounts of $CH_2FCF_2CF_2CHF_2$ (HFC-347pcc), $CHF_2CF_2CF_2CF_3$ (HFC-329p), $CH_3CF_2CF_2CF_3$ (HFC-347s) and $CH_2FCF_2CF_2CF_3$ (HFC-338q). Typically the selectivity to HFC-338pcc is at least 80%, preferably, at least 90% based upon the moles of HFC-374scc reacted.

Among the compounds produced during the preparation of HFC-338pcc from HFC-374scc by the process described above which are likely to form azeotropes with HF are $CCl_2FCF_2CF_2CClF_2$ (CFC-317lcc), $CClF_2CF_2CF_2CClF_2$ (CFC-318lcc), $CClF_2CF_2CF_2CF_3$ (CFC-319l), $CHClFCF_2CF_2CClF_2$ (HCFC-327lcc), $CHF_2CF_2CF_2CClF_2$ (HCFC-328lcc), $CHClFCF_2CF_2CF_3$ (HCFC-328r), $CHF_2CF_2CF_2CF_3$ (HFC-329p), $CH_2FCF_2CF_2CF_3$ (HFC-338q), $CH_3CF_2CF_2CF_3$ (HFC-347s) and $CH_2FCF_2CF_2CHF_2$ (HFC-347pcc). Conventional decantation/distillation may be employed if further purification of the listed compounds is desired.

Moreover, a process for purification as provided herein may also be used. Hydrofluoroalkanes and chloro-precursors thereof are provided in the process for producing HFC-338pcc described above. Typically, these compounds as well as HFC-388pcc form azeotropes with HF, and the process for purification provided herein may be advantageously used for purification of these compunds from their HF azeotropes (e.g., a binary azeotrope of HFC-338pcc with HF). Examples of compounds which can be purified from their binary with HF by this purification process include compounds selected from the group consisting of $CHF_2CF_2CF_2CHF_2$, $CCl_2FCF_2CF_2CClF_2$, $CClF_2CF_2CF_2CClF_2$, $CClF_2CF_2CF_2CF_3$, $CHClFCF_2CF_2CClF_2$, $CHF_2CF_2CF_2CCl_2F$, $CHF_2CF_2CF_2CClF_2$, $CHClFCF_2CF_2CF_3$, $CHCl_2CF_2CF_2CF_3$, $CHF_2CF_2CF_2CF_3$, $CH_2FCF_2CF_2CF_3$, $CH_3CF_2CF_2CF_3$ and $CH_2FCF_2CF_2CHF_2$. Of note is a process wherein $CHF_2CF_2CF_2CHF_2$ is purified from a mixture which consists essentially of hydrogen fluoride in combination with an effective amount of $CHF_2CF_2CF_2CHF_2$ to form an azeotrope or azeotrope-like composition with hydrogen fluoride, said azeotropic composition containing from about 3.5 to 36.8 mole percent $CHF_2CF_2CF_2CHF_2$. Also of note is a process wherein HF is recovered from a product mixture including $CHF_2CF_2CF_2CHF_2$ formed by the reaction of $CClF_2CF_2CF_2CClF_2$ with hydrogen in the presence of HF; and wherein an azeotropic composition consisting essentially of from about 96.5 to 63.2 mole percent HF and about from 3.5 to 36.8 mole percent $CHF_2CF_2CF_2CHF_2$, is recovered and recycled to a reactor for said reaction of $CClF_2CF_2CF_2CClF_2$ and hydrogen in the presence of HF.

The present invention also provides compositions which consist essentially of hydrogen fluoride and an effective amount of $CHF_2CF_2CF_2CHF_2$ to form an azeotropic combination with hydrogen fluoride. By effective amount is meant an amount which, when combined with HF, results in the formation of an azeotrope or azeotrope-like mixture. As recognized in the art, an azeotrope or an azeotrope-like composition is an admixture of two or more different components which, when in liquid form under given pressure, will boil at a substantially constant temperature, which temperature may be higher or lower than the boiling temperatures of the individual components, and which will provide a vapor composition essentially identical to the liquid composition undergoing boiling.

An azeotrope is a liquid mixture that exhibits a maximum or minimum boiling point relative to the boiling points of surrounding mixture compositions. An azeotrope is homogeneous if only one liquid phase is present. An azeotrope is heterogeneous if more than one liquid phase is present. Regardless, a characteristic of minimum boiling azeotropes is that the bulk liquid composition is then identical to the vapor composition in equilibrium therewith, and distillation is ineffective as a separation technique. For the purpose of this discussion, azeotrope-like composition means a composition which behaves like an azeotrope (i.e., has constant-boiling characteristics or a tendency not to fractionate upon boiling or evaporation). Thus, the composition of the vapor formed during boiling or evaporation of such compositions is the same as or substantially the same as the original liquid composition. Hence, during boiling or evaporation, the liquid composition, if it changes at all, changes only to a minimal or negligible extent. This is to be contrasted with non-azeotrope-like compositions in which during boiling or evaporation, the liquid composition changes to a substantial degree.

Accordingly, the essential features of an azeotrope or an azeotrope-like composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotropic composition may change when the azeotrope or azeotrope-like liquid composition is subjected to boiling at different pressures. Thus an azeotrope or an azeotrope-like composition may be defined in terms of the unique relationship that exists among components or in terms of the compositional ranges of the components or in terms of exact weight percentages of each component of the composition characterized by a fixed boiling point at a specified pressure. It is also recognized in the art that various azeotropic compositions (including their boiling points at particular pressures) may be calculated (see, e.g., W. Schotte, Ind. Eng. Chem. Process Des. Dev. 1980, 19, pp 432–439). Experimental identification of azeotropic compositions involving the same components may be used to confirm the accuracy of such calculations and/or to modify the calculations for azeotropic compositions at the same or other temperatures and pressures.

Compositions may be formed which consist essentially of azeotropic combinations of hydrogen fluoride with $CHF_2CF_2CF_2CHF_2$. These include a composition consisting essentially of from about 96.5 to about 63.2 mole percent HF and from about 3.5 to 36.8 mole percent $CHF_2CF_2CF_2CHF_2$ (which forms an azeotrope boiling at a temperature from between about −40° C. and about 145° C. and a pressure between about 7.3 kPa and about 4115 kPa).

At atmospheric pressure, the boiling points of hydrofluoric acid and HFC-338pcc are about 19.5° C. and 44.3° C., respectively. However, the relative volatility at 125 kPa (18.1 psia) and 20° C. of HF and HFC-338pcc was found to be nearly 1.0 as 88.4 mole percent HF and 11.6 mole percent HFC-338pcc was approached. These data indicate that the use of conventional distillation procedures will not result in the separation of a substantially pure compound because of the low value of relative volatility of the compounds.

To determine the relative volatility of HF with each of HFC-338pcc, the so-called PTx Method was used. In this procedure, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on pages 124 to 126, the entire disclosure of which is hereby incorporated by reference. Samples of the vapor and liquid, or vapor and each of the two liquid phases under those conditions where two liquid phases exist, were obtained and analyzed to verify their respective compositions.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids", 4th Edition, publisher McGraw Hill, written by Reid, Prausnitz and Poling, on pages 241 to 387; and in "Phase Equilibria in Chemical Engineering", published by Butterworth Publishers, 1985, written by Stanley M. Walas, pages 165 to 244; the entire disclosure of each of the previously identified references are hereby incorporated by reference.

Without wishing to be bound by any theory or explanation, it is believed that the NRTL equation can sufficiently predict whether or not mixtures of HF and HFC-338pcc behave in an ideal manner, and can sufficiently predict the relative volatilities of the components in such mixtures. Thus, while HF has a good relative volatility compared to HFC-338pcc at low HFC-338pcc concentrations, the relative volatility becomes nearly 1.0 as 11.6 mole percent HFC-338pcc was approached at 20° C. This would make it impossible to separate HFC-338pcc from HF by conventional distillation from such a mixture. Where the relative volatility approaches 1.0 defines the system as forming a near-azeotrope. Where the relative volatility is 1.0 defines the system as forming an azeotrope.

It has been found that azeotropes of HF and HFC-338pcc are formed at a variety of temperatures and pressures. At a pressure of 18.1 psia (125 kPa) and 20° C., the azeotrope vapor composition was found to be about 88.4 mole percent HF and about 11.6 mole percent HFC-338pcc. At a pressure of 69.2 psia (477 kPa) and 60° C., the azeotrope vapor composition was found to be about 81.6 mole percent HF and 18.4 mole percent HFC-338pcc. Based upon the above findings, it has been calculated that an azeotropic composition of about 96.5 mole percent HF and about 3.5 mole percent HFC-338pcc can be formed at −40° C. and 1.06 psia (7.3 kPa) and an azeotropic composition of about 63.2 mole percent HF and about 36.8 mole percent HFC-338pcc can be formed at 145° C. and 597 psia (4115 kPa). Accordingly, the present invention provides an azeotrope or azeotrope-like composition consisting essentially of from about 96.5 to 63.2 mole percent HF and from about 3.5 to 36.8 mole percent HFC-338pcc, said composition having a boiling point from about −40° C. at 7.3 kPa to about 145° C. at 4115 kPa.

The HFC-338pcc/HF azeotrope is useful as recycle to the fluorination reactor, where the recycled HF can function as a reactant and the recycled HFC-338pcc can function to moderate the temperature effect of the heat of reaction. It will also be apparent to one of ordinary skill in the art that distillation including azeotropes with HF can typically be run under more convenient conditions than distillation without HF, e.g., where HF is removed prior to distillation. HF may be removed from the halogenated hydrocarbon components of the product mixture using conventional aqueous solution scrubbing techniques. However, the production of substantial amounts of scrubbing discharge can create aqueous waste disposal concerns. Thus, there remains a need for processes utilizing HF in such product mixtures.

While the initial mixture treated in accordance with the present invention can be obtained from a variety of sources, including by adding HFC-338pcc to HF-containing compositions, an advantageous use of the instant invention resides in treating the effluent mixtures from the preparation of HFC-338pcc as described above. Generally, the reaction effluents have a molar ratio of HF:HFC-338pcc from about 0.1:1 to about 100:1. The preferred HF:HFC-338pcc molar ratio is from about 1:1 to 10:1 for vapor phase fluorination reactions and about 1:1 to about 50:1 for liquid phase reactions. The most preferred HF:HFC-338pcc molar ratio is from about 2:1 to 5:1 to achieve maximum benefit from the instant process. When the initial mixture treated in accordance with the invention also contains HCl and other low-boilers (e.g., $CHF_2CF_2CF_2CF_3$), the HCl and other low-boilers are removed in another distillation column before feeding the mixture to the azeotrope separation columns.

High-boilers, if present, can be removed in an independent distilation column after separation of HF from HFC-338pcc.

FIG. 1 is illustrative of one method of practicing this invention. Referring to FIG. 1, a feed mixture, derived from an HCFC-338pcc synthesis reactor, comprising HF and HFC-338pcc, wherein the molar ratio of HF:HFC-338pcc is greater than about 3:1, preferably greater than about 4:1, from an HCl removal column (not shown), is passed through line (426) to a multiple stage distillation column (410) operating at a temperature of about 100° C. and a pressure of about 1480 kPa. The bottoms of the distillation column (410) which contains HF at a temperature of about 115° C. and a pressure of about 1500 kPa is removed through line (436) and can be recycled back to the HFC-338pcc synthesis reactor. The distillate from column (410) which contains HF/HFC-338pcc azeotrope (HF:HFC-338pcc molar ratio is about 3:1) is removed from the top of the column (410) and sent through line (435) to column (420). The distillate from column (420) which contains HF/HFC-338pcc azeotrope (HF:HFC-338pcc molar ratio is about 7:1) and is at a temperature of about 20° C. and a pressure of about 140 kPa is removed from the top of column (420) and is recycled through line (445) to column (410). The bottoms of the distillation column (420) which contain essentially pure HFC-338pcc at about 57° C. and 156 kPa is removed from the bottom of the column (420) through line (446). In this embodiment column (410) operates as a high pressure column. Column (420) operates as a low pressure column.

In another embodiment of this invention the pressures of the columns are reversed. Again referring to FIG. 1, a feed mixture, derived from an HFC-338pcc synthesis reactor, wherein the HF:HFC-338pcc molar ratio in the feed mixture is about 3:1 or less, from an HCl removal column (not shown), is passed through line (426) to a multiple stage distillation column (410), operating at a temperature of about 20° C. and a pressure of about 140 kPa. The bottoms of the distillation column (410) which contain essentially pure HFC-338pcc at a temperature of about 57° C. and and a pressure of about 156 kPa is removed from the bottom of column (410) through line (436). The distillate from column (410) which contains HF/HFC-338pcc azeotrope (HF:HFC-338pcc molar ratio is about 7:1) at a temperature of about 20° C. and a pressure of about 140 kPa is removed from the top of column (410) and sent through line (435) to column (420). The distillate from column (420) which contains HF/HFC-338pcc azeotrope (HF:HFC-338pcc molar ratio is about 3:1) and is at a temperature of about 100° C. and a pressure of about 1480 kPa is removed from the top of column (420) and is recycled through line (445) to column (410). The bottoms of the distillation column (420) which contain HF at a temperature of about 115° C. and a pressure of about 1500 kPa is removed through line (446) and can be recycled back to the HFC-338pcc synthesis reactor. In this embodiment column (410) operates as a low pressure column. Column (420) operates as a high pressure column.

While specific temperatures, pressures and molar ratios were recited in the above two embodiments, variation of the pressure will also cause shifts in the HF:HFC-338pcc molar ratios and in the distillation temperatures. The use of a "low" and a "high" pressure column in tandem as described above can be used to separate HF from HFC-338pcc for any HF:HFC-338pcc ratio (e.g., from 0.1:1 to 100:1).

Those skilled in the art will recognize that since the drawings are representational, it will be necessary to include further items of equipment in an actual commercial plant, such as pressure and temperature sensors, pressure relief and control valves, compressors, pumps, storage tanks and the like. The provision of such ancillary items of equipment would be in accordance with conventional chemical engineering practice.

The distillation equipment and its associated feed lines, effluent lines and associated units should be constructed of materials resistant to hydrogen fluoride, hydrogen chloride and chlorine. Typical materials of construction, well-known to the fluorination art, include stainless steels, in particular of the austenitic type, and the well-known high nickel alloys, such as Monel® nickel-copper alloys, Hastelloy® nickel-based alloys and, Inconel® nickel-chromium alloys. Also suitable for reactor fabrication are such polymeric plastics as polytrifluoro-chloroethylene and polytetrafluoroethylene, generally used as linings.

Without further elaboration, it is believed that one skilled in the art can, using the description herein, utilize the present invention to its fullest extent. The following preferred specific embodiments are, therefore, to be construed as merely illustrative, and does not constrain the remainder of the disclosure in any way whatsoever.

EXAMPLES

Examples 1 to 5 and Comparative Examples A and B

Hydrogenolysis of HCFC-328lcc to HCFC-338pcc in the Presence of HF

Legend
HCFC-328lcc or 328lcc is $CHF_2CF_2CF_2CClF_2$
HFC-338pcc or 338pcc is $CHF_2CF_2CF_2CHF_2$
HP is high pressure.
LP is low pressure.

The carbon support used in the examples was a 4×8 mesh (about 4.7 mm×2.4 mm) commercial grade coconut shell carbon which had (before washing) an ash content of about 2.6 weight percent. After hydrochloric acid washing, the carbon support had an ash content of less than about 0.1 weight percent.

Liquid HCFC-328lcc (analysis: 93.3% 328lcc and 6.7% unknowns), 3 mL/hour, was vaporized and mixed with 20 cc/minute of hydrogen and either 0, 5 or 10 mL/minute of HF. This vapor mixture was sent through a 0.5" (12.7 mm) O.D.×8" (203 mm) Hastelloy® nickel alloy reactor containg 5.0 g of 0.5 weight percent palladium supported on acid-washed carbon maintained at the various temperatures shown in Table 1 using a fluidized sand bath. Only a small portion of the total reactor effluent was sent to the gas chromatograph for organic product analysis. The bulk of the product stream which also contains inorganic acids such as HCl and HF was sent to a caustic scrubber for neutralization of the acids. A sample of the product stream was analyzed using gas chromatography. Results of these in analysis, in area % are shown in Table 1.

TABLE 1

| Ex. | Temp. °C. | HF mL/min. | Unknowns area % | 3281 cc area % | 338 ppc area % |
|---|---|---|---|---|---|
| FEED | — | — | 6.7 | 93.3 | 0.0 |
| 1 | 200 | 5 | 4.5 | 74.3 | 21.1 |
| 2 | 200 | 10 | 4.0 | 75.3 | 20.7 |
| A | 200 | — | 4.8 | 74.9 | 20.3 |
| 3 | 250 | 10 | 5.7 | 9.8 | 84.5 |
| B | 250 | — | 5.4 | 10.4 | 84.3 |
| 4 | 275 | 10 | 8.2 | 0.6 | 91.2 |
| 5 | 300 | 10 | 9.8 | 0.0 | 90.2 |

Examples 6 and 7

In the following two examples, all values for the compounds are in moles and temperatures are in Celsius. The data were obtained by calculation using measured and calculated thermodynamic properties. The numbers at the top of the columns refer to FIG. 1.

| | EXAMPLE 6 | | | | |
|---|---|---|---|---|---|
| Compound | 426 Feed Mixture | 435 HP Col. Dist. | 436 Recycle HF | 445 HF/338 pcc Recycle | 446 338 pcc Prod. |
| HF | 83.3 | 86.5 | 83.3 | 86.5 | — |
| 338 pcc | 16.7 | 28.7 | 0.08 | 12.1 | 16.6 |
| Temp. °C. | 102 | 102 | 115 | 22 | 57 |
| Press. kPa | 1480 | 1480 | 1500 | 136 | 156 |

| | EXAMPLE 7 | | | | |
|---|---|---|---|---|---|
| Compound | 426 Feed Mixture | 435 LP Col. Dist. | 436 338 pcc Prod. | 445 HP Col. Dist. | 446 Recycle HF |
| HF | 33.3 | 57.3 | — | 23.9 | 33.3 |
| 338 pcc | 16.7 | 8.0 | 16.6 | 7.9 | 0.08 |
| Temp. °C. | 22 | 22 | 22 | 102 | 115 |
| Press. kPa | 136 | 136 | 136 | 1480 | 1500 |

What is claimed is:
1. A process for producing 1,1,2,2,3,3,4,4-octafluorobutane, comprising:

(a) reacting a mixture comprising 2,2,3,3-tetrafluorobutane and chlorine to form a mixture of chloro-compounds selected from the group consisting of $CCl_3(CF_2)_2CCl_3$, $CHCl_2(CF_2)_2CCl_3$, $CH_2Cl(CF_2)_2CCl_3$, $CH_3(CF_2)_2CCl_3$, $CH_3(CF_2)_2CHCl_2$ and $CH_3(CF_2)_2CH_2Cl$ wherein compounds of the formula $C_4H_xCl_{6-x}F_4$, where x is 0 or 1, comprise at least about 50 mole % of said mixture of chloro-compounds;

(b) contacting a mixture comprising compounds of the formula $C_4H_xCl_{6-x}F_4$ from (a) and hydrogen fluoride with a fluorination catalyst to form a mixture of fluoro-compounds selected from the group consisting of $CCl_2F(CF_2)_2CCl_3$, $CCl_2F(CF_2)_2CCl_2F$, $CCl_2F(CF_2)_2CClF_2$, $CClF_2(CF_2)_2CClF_2$, $CClF_2(CF_2)_2CF_3$, $CHCl_2(CF_2)_2CCl_2F$, $CHClF(CF_2)_2CCl_3$, $CHCl_2(CF_2)_2CClF_2$, $CHClF(CF_2)_2CCl_2F$, $CHF_2(CF_2)_2CCl_3$, $CHClF(CF_2)_2CClF_2$, $CHF_2(CF_2)_2CCl_2F$, $CHCl_2(CF_2)_2CF_3$, $CHClF(CF_2)_2CF_3$, $CHF_2(CF_2)_2CClF_2$ and $CHF_2(CF_2)_2CF_3$ wherein compounds of the formula $C_4H_{2-y}Cl_yF_8$, where y is 1 or 2, comprise at least about 10 mole % of said mixture of fluoro-compounds; and (c) contacting a mixture comprising compounds of the formula $C_4H_{2-y}Cl_yF_8$ from (b) and hydrogen with a hydrogenolysis catalyst to produce $CHF_2CF_2CF_2CHF_2$; sufficient chloro-compounds formed in (a) being recycled to the chlorination of (a) and sufficient fluoro-compounds formed in (b) being recycled to the chlorination of (a) or the fluorination of (b) to provide a selectivity to $CHF_2CF_2CF_2CHF_2$ of at least about 75% based upon the moles of $CH_3CF_2CF_2CH_3$ reacted in (a).

2. A process for the purification of $CHF_2CF_2CF_2CHF_2$ from a mixture comprising HF and $CHF_2CF_2CF_2CHF_2$ produced by the process of claim 1, comprising (a) subjecting the mixture of HF and $CHF_2CF_2CF_2CHF_2$ to a distillation step in which a composition enriched in either (i) HF or (ii) $CHF_2CF_2CF_2CHF_2$ is removed as a first distillate with the bottoms being enriched in the other of said components (i) or (ii);

(b) subjecting said first distillate to an additional distillation conducted at a different pressure in which the component enriched as bottoms in (a) is removed as a second distillate with the bottoms of the additional distillation enriched in the components enriched in the first distillate; and (c) recovering said $CHF_2CF_2CF_2CHF_2$ essentially free of HF as bottoms from either the distillation of step (a) or the distillation of step (b).

3. The process of claim 2 wherein said mixture consists essentially of hydrogen fluoride in combination with an effective amount of $CHF_2CF_2CF_2CHF_2$ to form an azeotrope or azeotrope-like composition with hydrogen fluoride, said azeotropic composition containing from about 3.5 to 36.8 mole percent $CHF_2CF_2CF_2CHF_2$.

4. A compound selected from the group consisting of $CCl_2FCF_2CF_2CClF_2$, $CCl_3CF_2CF_2CCl_2F$, $CHCl_2CF_2CF_2CCl_3$, $CHCl_2CF_2CF_2CCl_2F$, $CHClFCF_2CF_2CCl_3$, $CHCl_2CF_2CF_2CClF_2$, $CHClFCF_2CF_2CCl_2F$, $CHF_2CF_2CF_2CCl_3$, $CHF_2CF_2CF_2CCl_2F$, $CHClFCF_2CF_2CF_3$, $CH_3CF_2CF_2CH_2Cl$ and $CH_2ClCF_2CF_2CCl_3$.

5. The compound of claim 4 which is $CCl_2FCF_2CF_2CClF_2$.

6. The compound of claim 4 which is $CCl_3CF_2CF_2CCl_2F$.

7. The compound of claim 4 which is $CHCl_2CF_2CF_2CCl_3$.

8. The compound of claim 4 which is $CHCl_2CF_2CF_2CCl_2F$.

9. The compound of claim 4 which is $CHClFCF_2CF_2CCl_3$.

10. The compound of claim 4 which is $CHCl_2CF_2CF_2CClF_2$.

11. The compound of claim 4 which is $CHClFCF_2CF_2CCl_2F$.

12. The compound of claim 4 which is $CHF_2CF_2CF_2CCl_3$.

13. The compound of claim 4 which is $CHF_2CF_2CF_2CCl_2F$.

14. The compound of claim 4 which is $CHClFCF_2CF_2CF_3$.

15. The compound of claim 4 which is $CH_3CF_2CF_2CH_2Cl$.

16. The compound of claim 4 which is $CH_2ClCF_2CF_2CCl_3$.

* * * * *